US009459186B2

(12) United States Patent
Mastromatteo et al.

(10) Patent No.: US 9,459,186 B2
(45) Date of Patent: Oct. 4, 2016

(54) SAMPLE PREPARATION AND LOADING MODULE

(71) Applicant: STMicroelectronics S.r.l., Agrate Brianza (IT)

(72) Inventors: Ubaldo Mastromatteo, Bareggio (IT); Flavio Francesco Villa, Milan (IT); Gabriele Barlocchi, Cornaredo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 483 days.

(21) Appl. No.: 13/858,156

(22) Filed: Apr. 8, 2013

(65) Prior Publication Data

US 2013/0273548 A1 Oct. 17, 2013

(30) Foreign Application Priority Data

Apr. 12, 2012 (IT) .................... TO2012A0320

(51) Int. Cl.
| | |
|---|---|
| *G01N 1/28* | (2006.01) |
| *C12N 15/10* | (2006.01) |
| *B01L 3/00* | (2006.01) |
| *G01N 1/40* | (2006.01) |
| *C12Q 1/68* | (2006.01) |

(52) U.S. Cl.
CPC ............ *G01N 1/28* (2013.01); *B01L 3/502* (2013.01); *C12N 15/1017* (2013.01); *C12Q 1/6806* (2013.01); *G01N 1/405* (2013.01); *B01L 3/5027* (2013.01); *B01L 2300/0681* (2013.01); *B01L 2300/0829* (2013.01); *B01L 2300/0864* (2013.01); *B01L 2300/0867* (2013.01); *B01L 2400/0478* (2013.01); *B01L 2400/0616* (2013.01)

(58) Field of Classification Search
None
See application file for complete search history.

(56) References Cited

U.S. PATENT DOCUMENTS

| | | | |
|---|---|---|---|
| 5,976,824 A | 11/1999 | Gordon | |
| 2004/0086872 A1* | 5/2004 | Childers | ........... B01L 3/502707 435/6.19 |
| 2004/0155213 A1* | 8/2004 | Yoo | ................................ 251/65 |
| 2004/0232080 A1* | 11/2004 | Neyer et al. | .................. 210/656 |

(Continued)

FOREIGN PATENT DOCUMENTS

| | | | |
|---|---|---|---|
| AU | WO 2012073115 A1 * | 6/2012 | ........ B01L 3/502707 |
| CN | 2724003 Y | 9/2005 | |
| IT | IO 31029 | 12/2012 | |

OTHER PUBLICATIONS

Han et al. An automated micro-solid phase extraction device involving integrated high-pressure microvalves for genetic sample preparation. Biomed Microdevices 11:935-942 (2009).*

(Continued)

*Primary Examiner* — Samuel Woolwine
(74) *Attorney, Agent, or Firm* — Seed IP Law Group PLLC

(57) ABSTRACT

The device has a fluid inlet; a filtering compartment, connected to the fluid inlet and accommodating a filtering matrix in presence of adsorption agents; a fluidic circuit connected downstream of the filtering compartment and including a discharge circuit and a loading circuit; a discharge chamber, connected downstream of the discharge circuit; a preparation outlet, connected downstream of the loading circuit; and suction pumps, connected to the fluidic circuit and configured so as to fluidically connect the filtering compartment alternatively to the discharge circuit or to the loading circuit.

28 Claims, 12 Drawing Sheets

(56) References Cited

U.S. PATENT DOCUMENTS

| | | | |
|---|---|---|---|
| 2005/0142565 A1 | 6/2005 | Samper et al. | |
| 2006/0222569 A1* | 10/2006 | Barten | B01L 3/502 |
| | | | 422/400 |
| 2006/0285430 A1* | 12/2006 | Seto | 366/163.1 |
| 2007/0196833 A1 | 8/2007 | Gjerde et al. | |
| 2008/0057572 A1* | 3/2008 | Petersen | B01L 3/502 |
| | | | 435/306.1 |
| 2008/0096192 A1 | 4/2008 | Nurmi et al. | |
| 2010/0068706 A1* | 3/2010 | Pourahmadi et al. | 435/6 |
| 2010/0297754 A1* | 11/2010 | Solli | B01L 3/5027 |
| | | | 435/325 |
| 2011/0236273 A1 | 9/2011 | Claussen et al. | |
| 2012/0048734 A1* | 3/2012 | Sugiyama | G01N 35/1095 |
| | | | 204/453 |

OTHER PUBLICATIONS

PTC-200 Operations Manual from MJ Research (1999).*
Xu et al. A self-contained polymeric cartridge for automated biological sample preparation. Biomicrofluidics 5:034107-1-9 (2011).*
Krusemark et al. Micro ball valve for fluidic micropumps and gases. Micro TAS '98, pp. 399-402 (1998).*

* cited by examiner

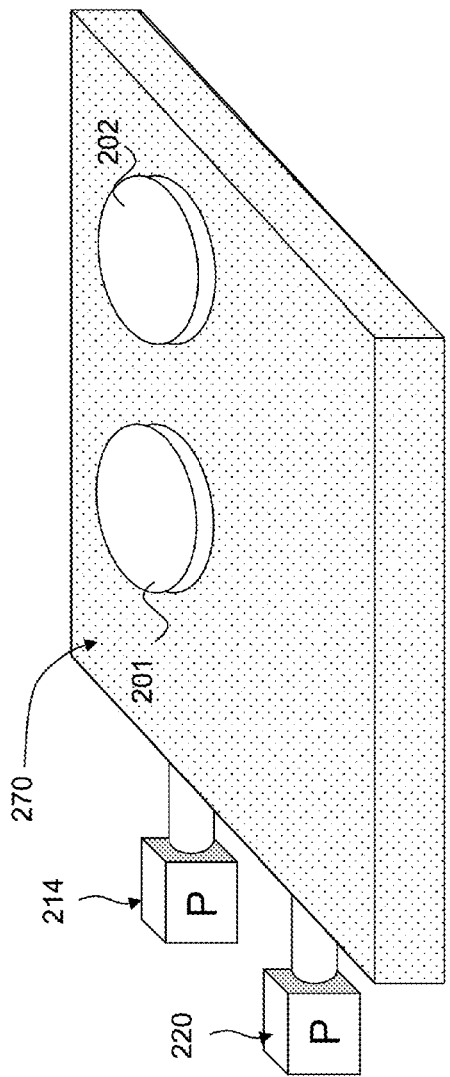
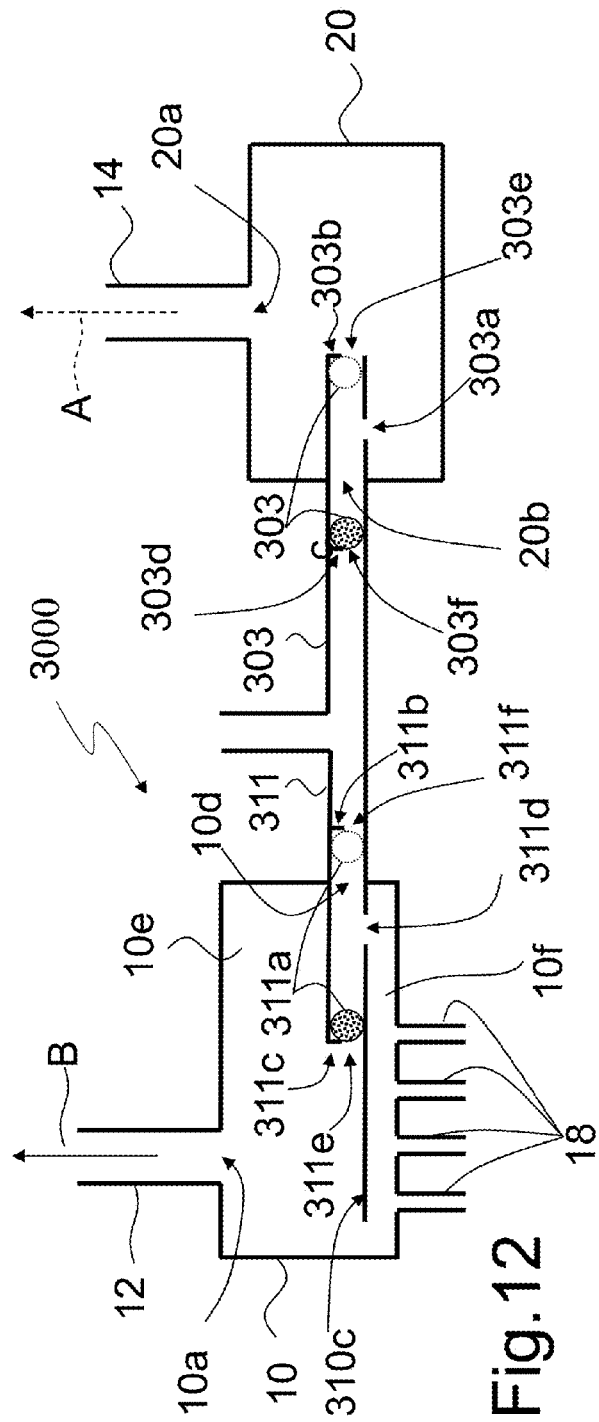
Fig. 11
Fig. 12

SAMPLE PREPARATION AND LOADING MODULE

CROSS-REFERENCE TO RELATED APPLICATIONS

This application claims priority to Italian Application Number TO2012A000320, filed Apr. 12, 2012, incorporated by reference in its entirety.

TECHNICAL FIELD

The present disclosure relates to a device and a method for preparing biologic samples to render the prepared sample suitable for use in subsequent processes of analysis, particularly in lab-on-chip devices.

BACKGROUND

An example of preparation of a sample consists of extracting and subsequently purifying biological material for use in subsequent analysis. Preparation of the biologic sample, including extraction of DNA and subsequent purification, also referred to as "sample preparation", is the starting point of numerous processes of DNA analysis, such as RT-PCR, electrophoresis, genotyping, etc.

Currently, sample preparation can be performed using suitable kits available on the market, which are operated manually performing a particular procedure. FIG. 1 illustrates the so-called "spin-column method" that is among the most widely used sample-preparation procedures. With reference to FIG. 1, the process implemented by this method includes four steps.

In a first step, referred to as "pretreatment", the selected biologic sample, from which the DNA is to be extracted, for example whole blood, is subjected to a cell lysis comprising dissolving the cell by disrupting the cell membrane. Lysis is carried out, e.g., by arranging the biologic sample in a hypotonic solution. After lysis, using suitable enzymes such as proteinase K, digestion of the contaminating proteins is performed.

The second step, referred to as "DNA binding", consists of the separation and recovery of the nucleic acid from the solution containing the lysed cell material. One of the most recent methods consists in the use of a matrix of silica gel in presence of chaotropic salts that adsorbs and binds the DNA.

In the third step, referred to as "washing", the gel matrix is washed using a suitable solution such as, for example, buffer and/or ethanol, in order to eliminate interfering residue, such as proteins and lipids.

In the fourth step, referred to as "elution", the silica-gel matrix, binding the DNA, is eluted using an aqueous solution with low saline concentration. By virtue of this treatment, the DNA previously captured on the surface of the gel matrix is removed and made available in a solution within the test tube. The prepared sample is ready for use in the downstream application, for example RT-PCR.

In order to carry out RT-PCR, the prepared sample is subsequently collected with a pipette and transferred into the wells provided in a silicon chip accommodated on a disposable cartridge. Next, this cartridge is inserted in a thermal cycler with a fluorescence detector for carrying out DNA analysis.

All of the previously described steps regarding preparation of the sample and loading of the prepared sample into the wells in a silicon chip are performed manually using the devices provided with the kit (test tubes, pipettes, buffers, etc.). The sequence of the various steps involves handling a large number of devices and transferring liquids in the transition from one step to the next of the method.

Because of the large number of manoeuvres and devices involved and the precision required in the manual manipulations, the method is particularly slow, cumbersome in its implementation, and exposed to accidental errors of execution and to contamination by the surrounding environment. Thereby it is, as a whole, far from robust and reliable in relation to the quality of the end result.

The method described above is moreover far from effective in terms of economic yield, requiring the use of large amounts of costly reagents. Finally, it can be carried out only by highly specialized staff, limiting use thereof to just the hospital and/or laboratory environment.

SUMMARY

The disclosure provides a device and a relevant method for preparing and for loading a sample containing biological material into wells within a silicon chip, suitable for subsequent use in an analysis. The device and the associated method for preparing a sample containing biological material has to be simple to implement, enable a high rapidity in preparation of the sample and thus short analysis times, have reduced costs, provide robustness in terms of quality of the end result, and finally be usable by staff that are not necessarily highly qualified. The step of loading the sample into the wells must be integratable with the device. In other words, the sample preparation and loading device should be modular, designed to integratingly fit into a lab-on-chip device such that sample transfer steps are eliminated once the device is loaded for the first time.

According to the present disclosure, a device, an apparatus, and a method for preparing a sample containing biological material are provided.

DESCRIPTION OF THE FIGURES

For a better understanding of the disclosure and the advantages thereof, some non-limiting embodiments are described hereinafter, with reference to the attached drawings, wherein:

FIG. 11 is a perspective view of the device for preparing the sample of FIG. 10.

FIG. 12 partially illustrates the vertical cross-section of a further embodiment of the present device.

DETAILED DESCRIPTION

Figure 1:
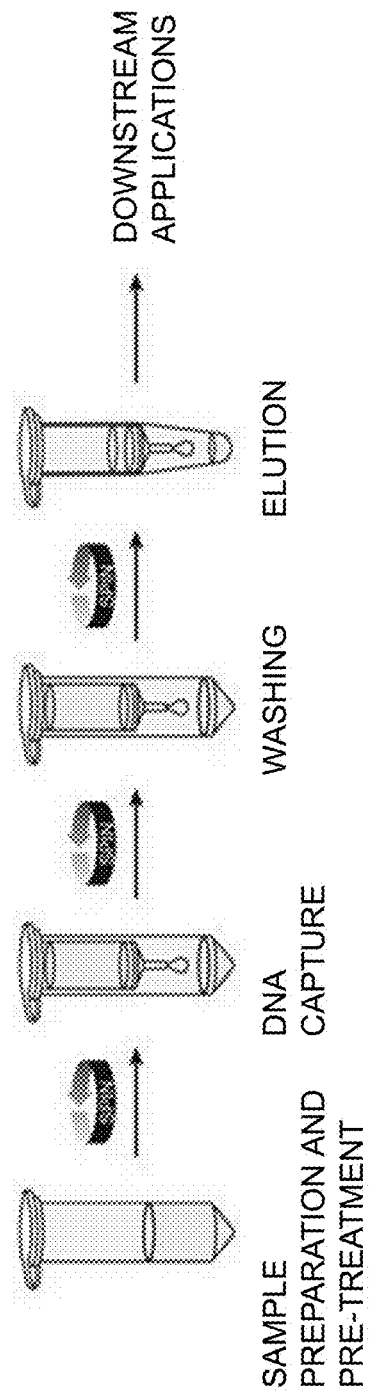
FIG. 1 illustrates the method of the prior art, known as "spin-column method", for preparing a sample, in particular for extracting and purifying DNA.
Figure 2:
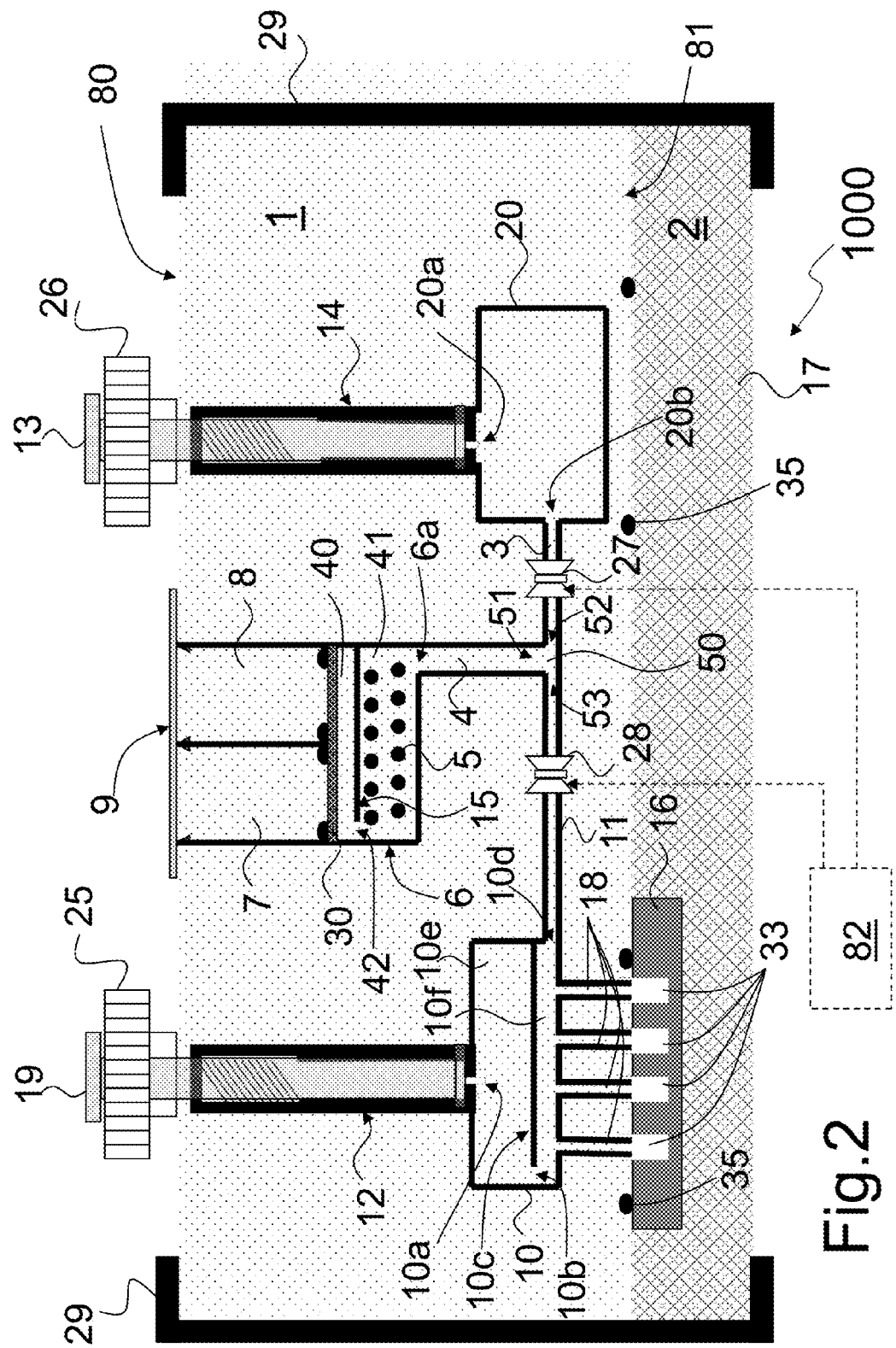
FIG. 2 shows a vertical cross-section of a first embodiment of a device for preparing a sample containing biological material.
Figure 3:
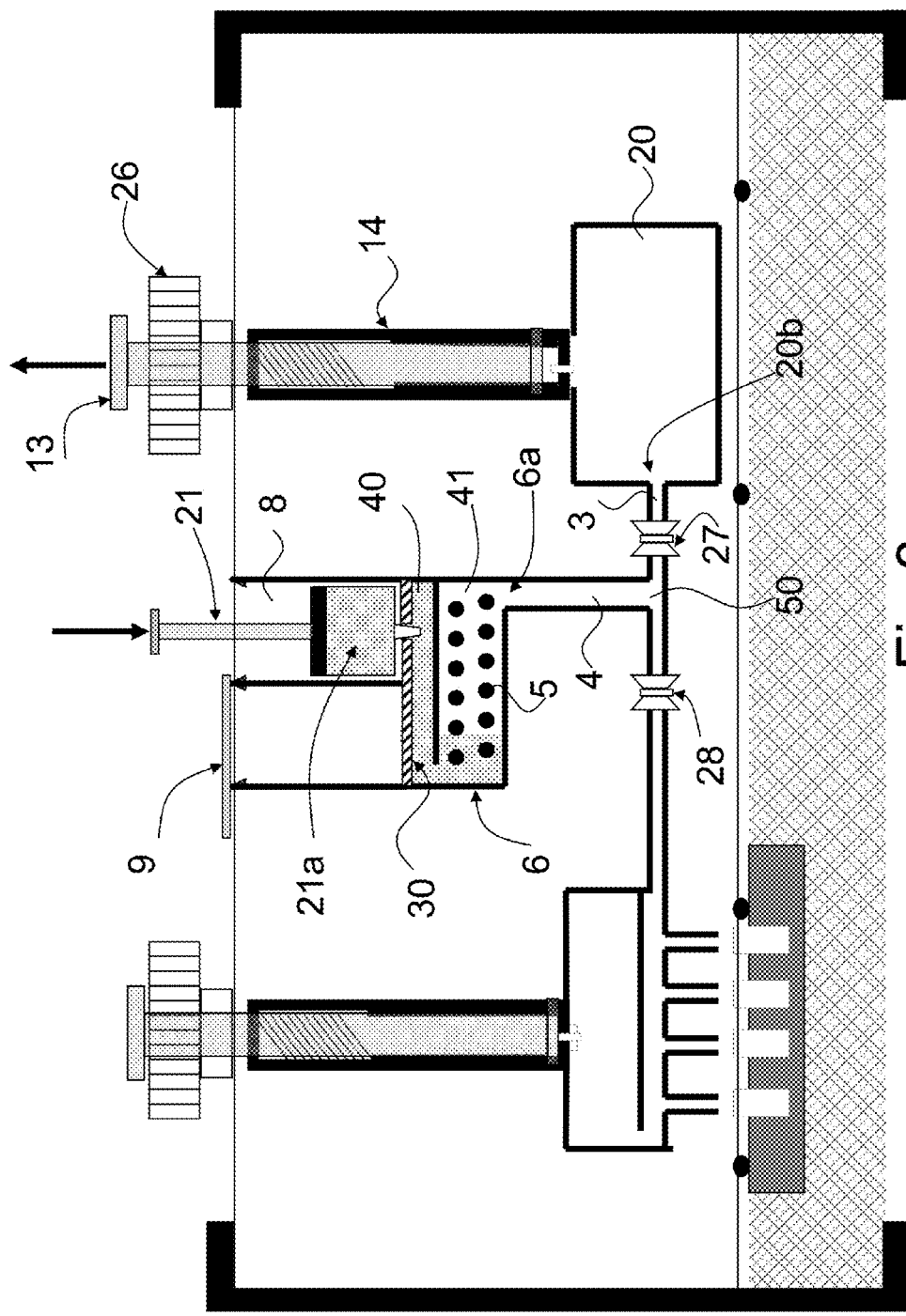
FIGS. 3-8 are vertical cross-sections of the device of FIG. 2 during successive steps of the method.
Figure 4:
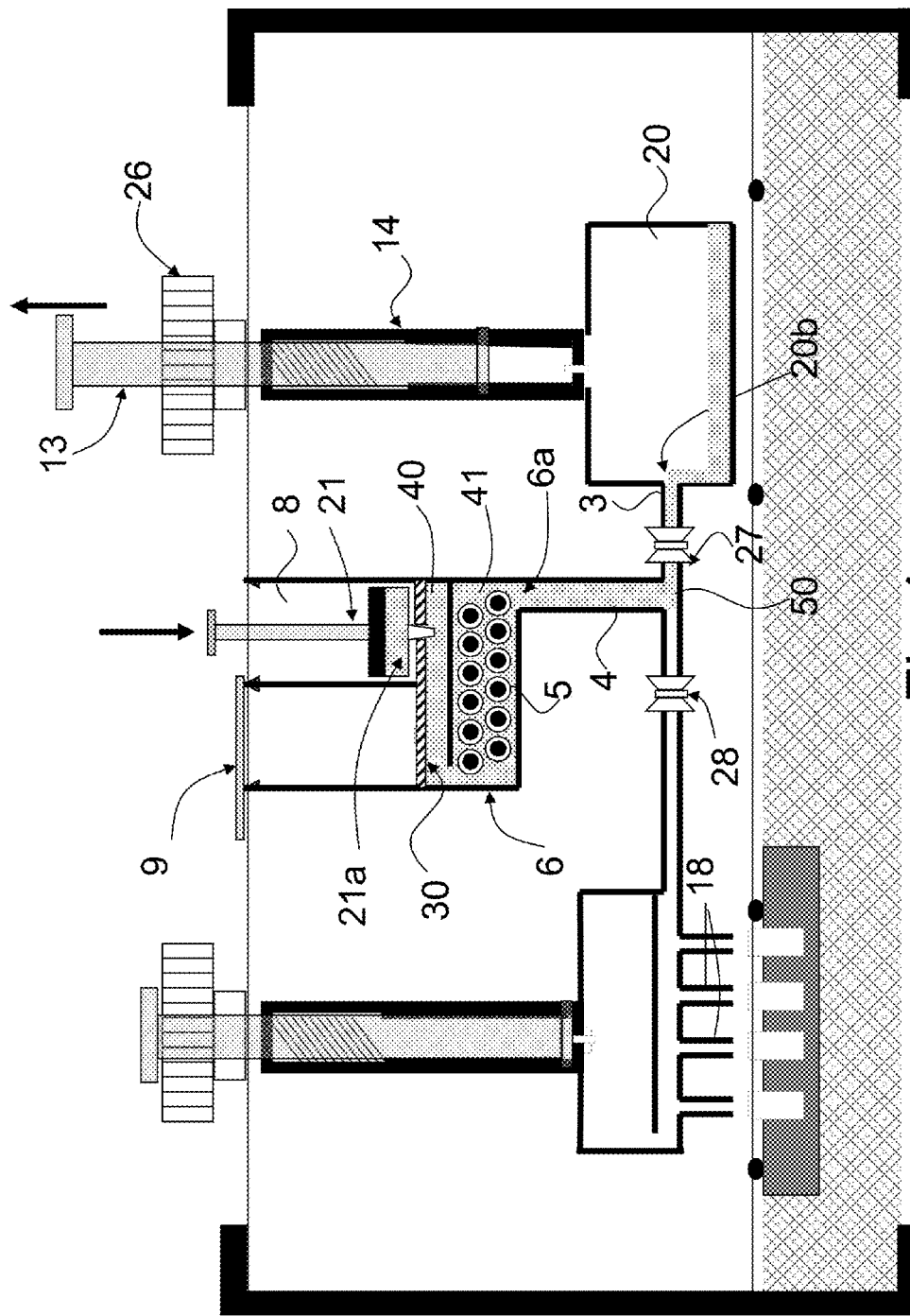
Figure 5:
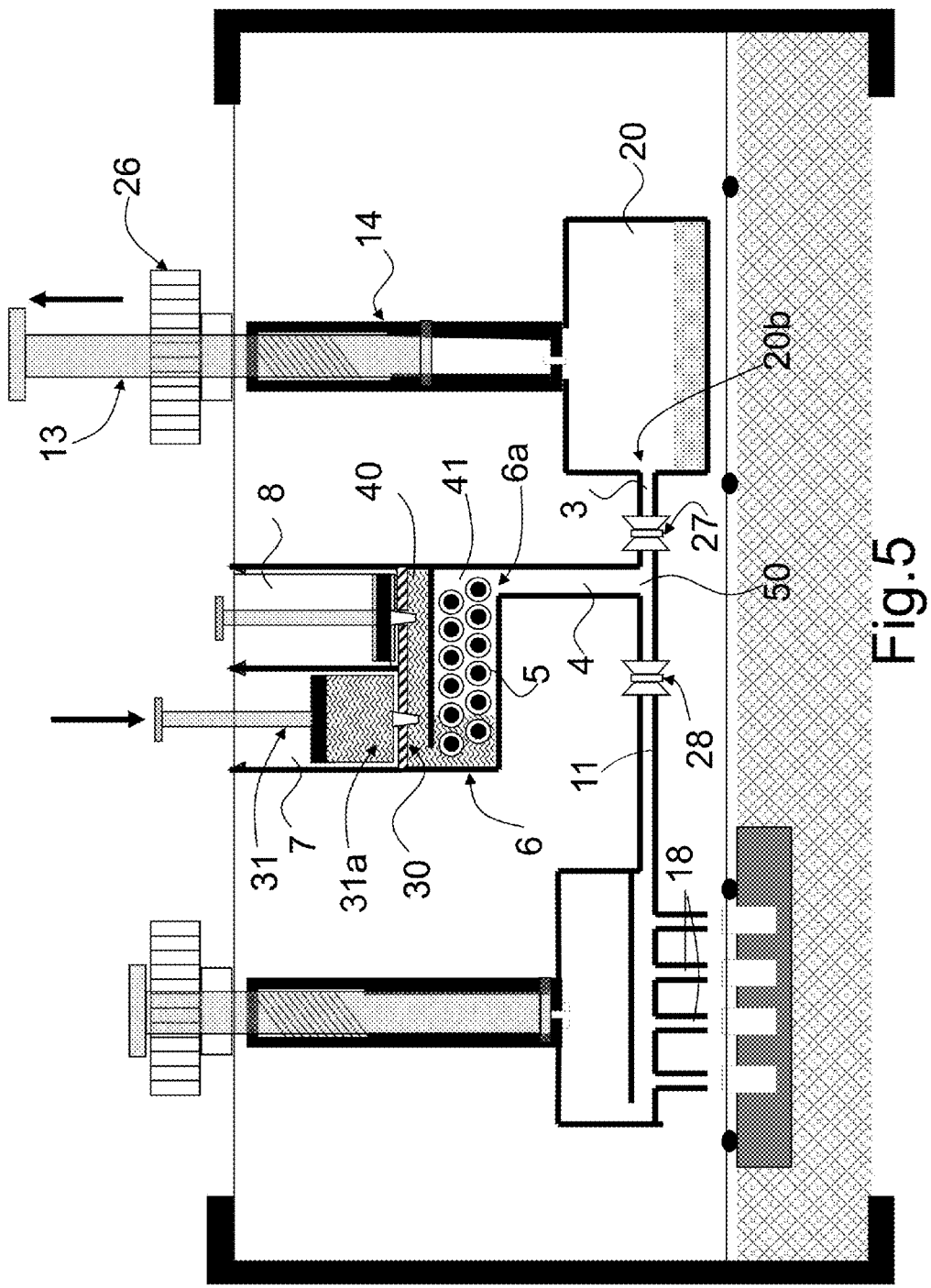
Figure 6:
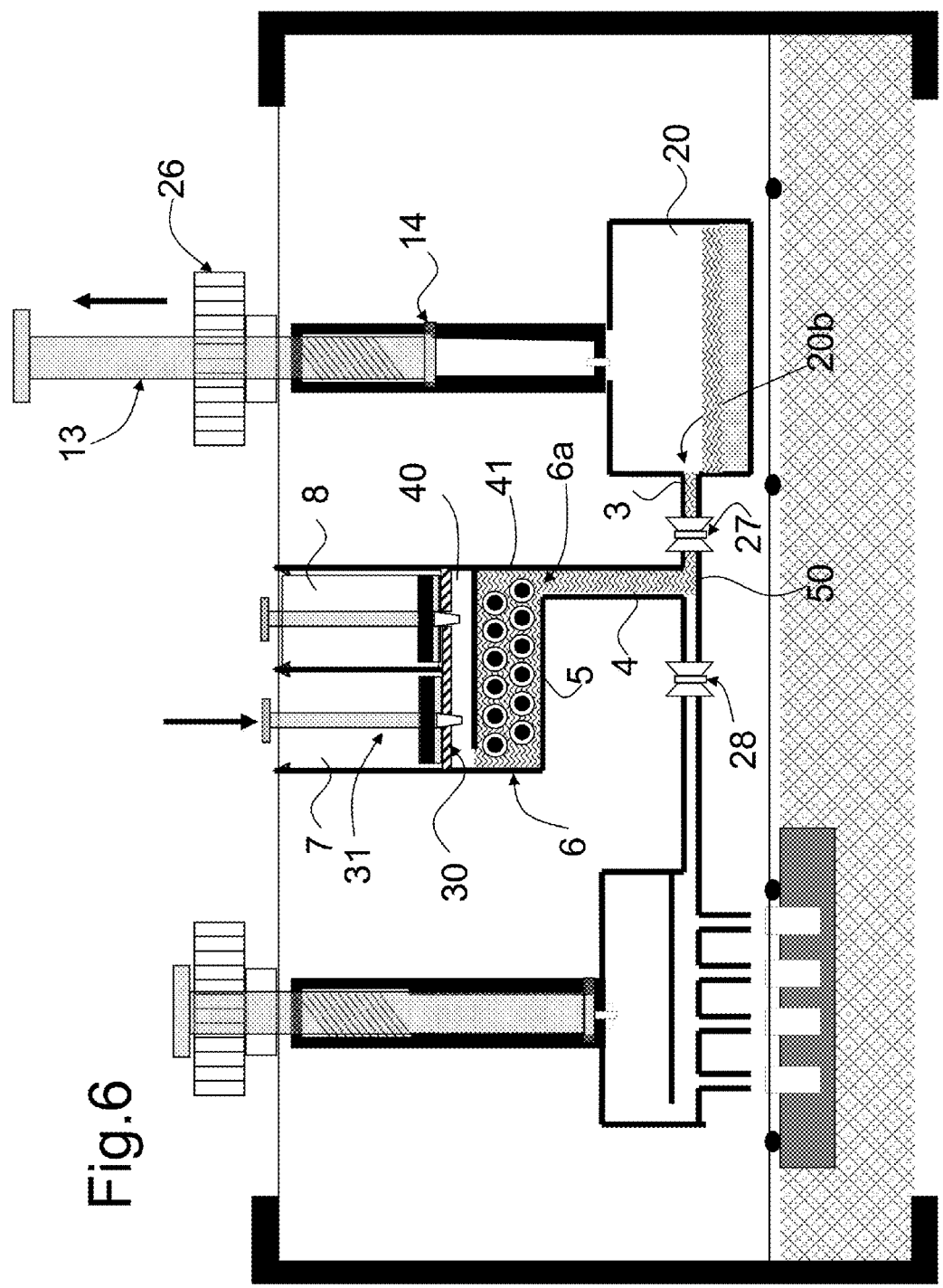
Figure 7:
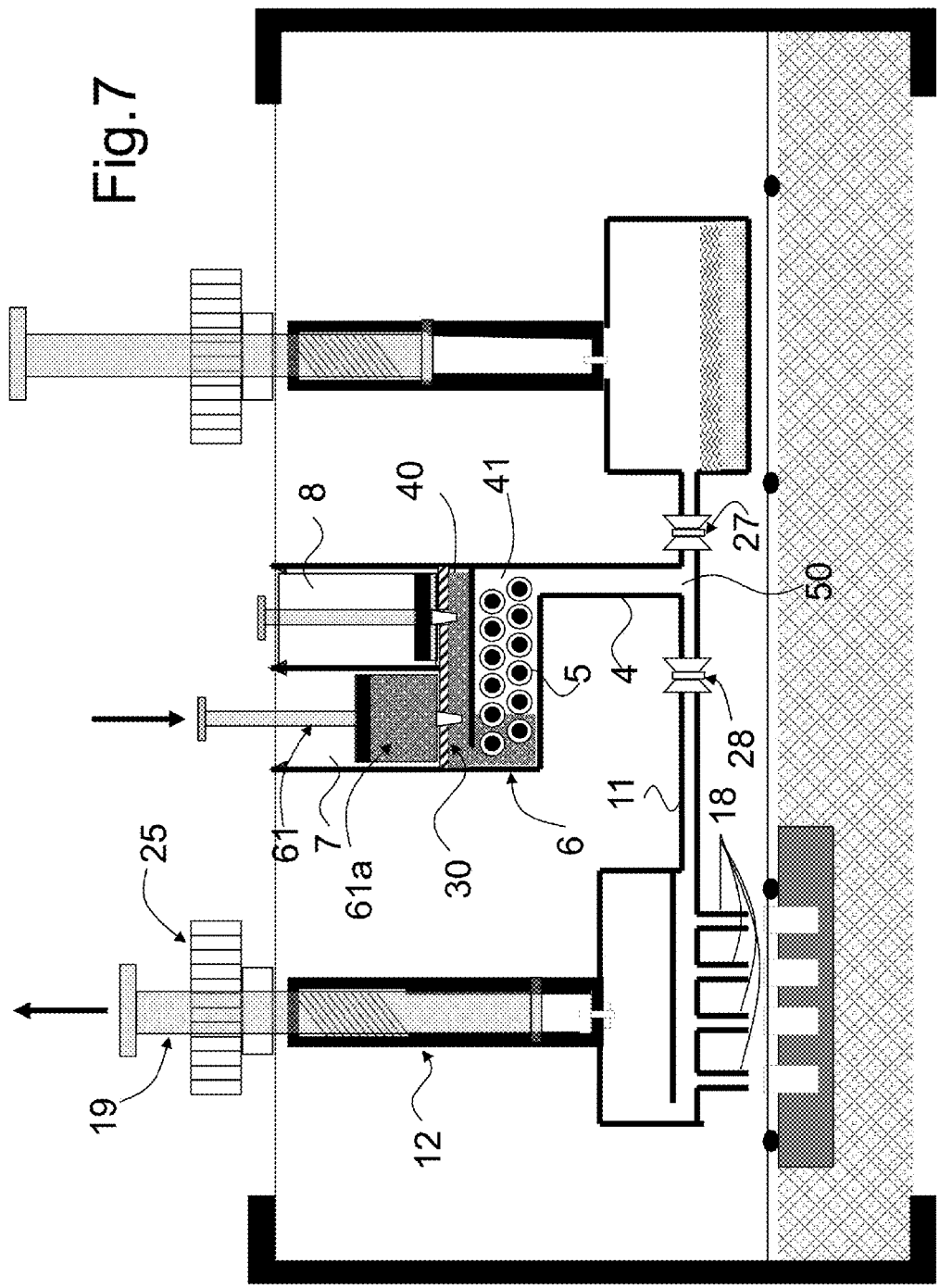
Figure 8:
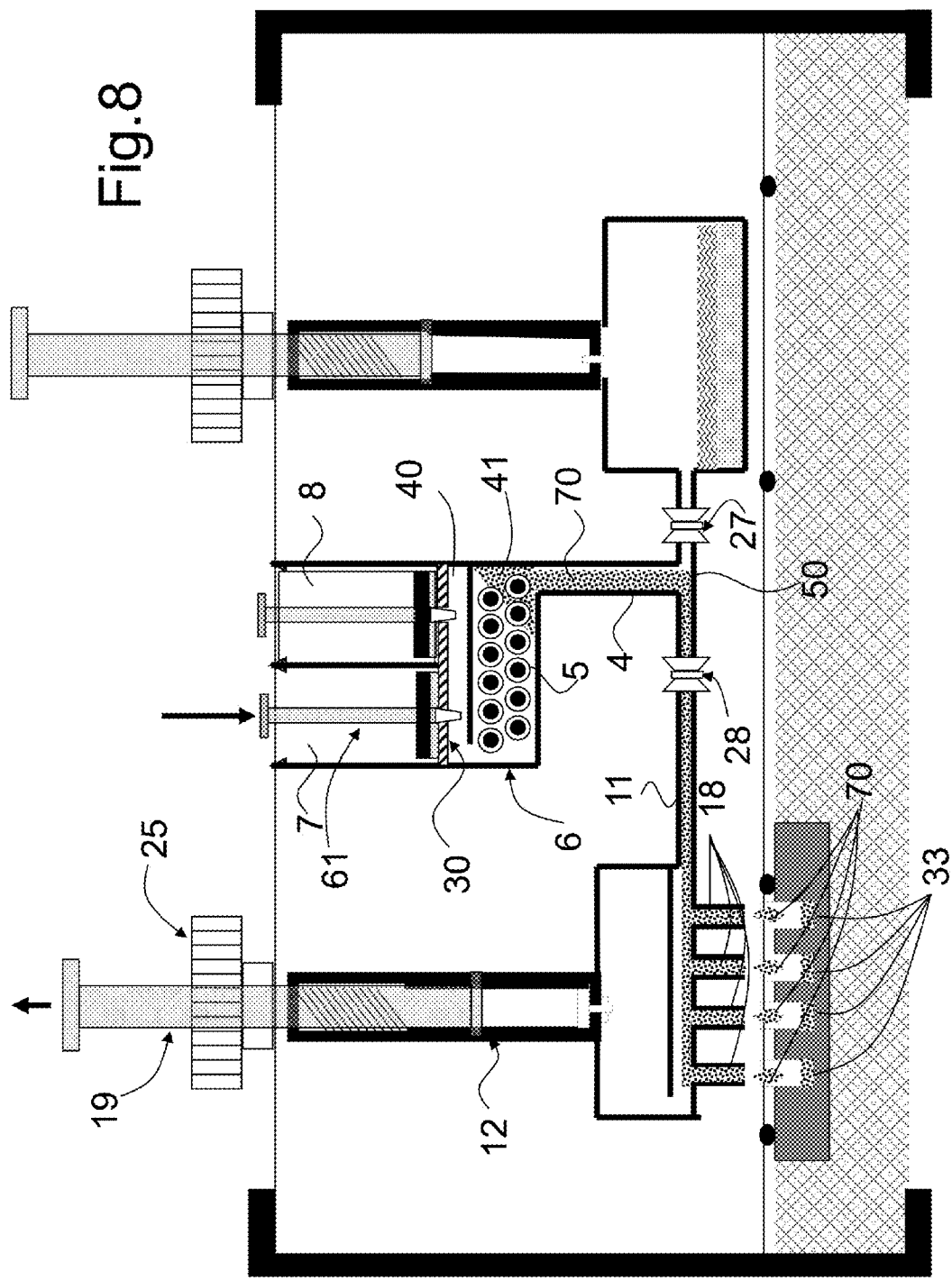

FIG. 2 illustrates an embodiment of a device 1000 of a disposable type for preparing a sample containing biological material, in particular for extracting DNA. The device 1000 comprises a body 1 for advancing the fluids and a cartridge 2 for RT-PCR (Real-Time Polymerase-Chain Reaction). Gaskets 35, for example of the O-ring type, are arranged between the body 1 and the cartridge 2 for ensuring tightness and preventing leakage.

For example, the body 1 can have a parallelepipedal shape, with dimensions of about 5×4×3 cm$^3$, so as to have an overall volume not greater than 60 cm$^3$.

The cartridge 2 comprises a support 17, for example of plastic material of the type used in the production of printed circuits, and a chip 16, for example of silicon, arranged in a cavity of the support 17 and provided with a plurality of wells 33, each of which may contain, for example, various primers and/or probes for parallel and/or multiplex analysis of the sample. The body 1 is made, for example, of partially or completely transparent plastic material, such as transparent polycarbonate manufactured using moulding and forging techniques. The body 1 and the cartridge 2 are fixed together by means of lateral clips 29.

The body 1 comprises fluid advancing means, here comprising two suction units, including a first piston housing 14, accommodating a first piston 13, and a second piston housing 12, accommodating a second piston 19. The first and second pistons 13 and 19 and the respective housings 14 and 12 are conformed so as to enable the first and second pistons 13, 19 to fluid-tightly slide within the housings 14 and 12, respectively.

The body 1 further comprises a first and a second syringe chambers 7, 8, each forming a fluid inlet, open towards the outside on a top surface 80 of the body 1, but sealed (prior to use) by an adhesive and perforatable outer closing layer 9, for example of aluminium, plasticized on the part in contact with the top surface 80. The bottom wall of the first and second chambers 7, 8 is defined by a diaphragm 30, for example having two plastic layers and an intermediate sealing and perforatable aluminium layer.

The body 1 further comprises a filtering compartment 6 arranged underneath the diaphragm 30 and accommodating a filtering matrix 5 (shown as black dots) in the presence of adsorption agents, for example silica gel in presence of chaotropic salts. In the embodiment shown, the top surface of the filtering compartment 6 is formed by the diaphragm 30. In use, the filtering compartment 6 is fluidically connected to the syringe chambers 7, 8 by tearing or perforating the diaphragm 30, as described in greater detail hereinafter.

According to an embodiment, the filtering compartment 6, for example, having a parallelepiped shape, accommodates a partial diaphragm 15, which extends transversely from the side walls of the filtering compartment, substantially parallel to the bottom base of the body 1, and occupies only partially a cross-section of the filtering compartment 6 that is parallel to the bottom base of the body 1, thus forming a connection opening 42. The partial diaphragm 15 divides the volume of the filtering compartment 6 into a conveying duct 40, which extends above the partial diaphragm 15, and a matrix compartment 41, which extends underneath the partial diaphragm 15 and accommodates the filtering matrix 5.

The conveying duct 40 and the matrix compartment 41 are fluidically connected to each other through the connection opening 42. The filtering compartment 6 further comprises an outlet opening 6a, arranged on the bottom base of the filtering compartment 6 and opening towards a fluidic circuit comprising a first, a second and a third communication ducts 3, 4, 11, as described in greater detail hereinafter.

In the embodiment shown in FIG. 2, the connection opening 42 and the outlet opening 6a are arranged on opposite sides of the compartment 6, so that the fluidic path that extends between the connection opening 42 and the outlet opening 6a has the maximum possible length. Thus, any fluid traversing from 42 to 6a travels the length of available filtering matrix 5.

The second communication duct 4 (forming, together with the first communication duct 3, a discharge circuit and, together with the third communication duct 11, a loading circuit) extends downwards from the outlet opening 6a as far as an inlet port 51 of a hydraulic T connector 50. The latter further has a first and a second outlet port 52, 53.

The first communication duct 3 extends from the first outlet port 52 of the hydraulic T connector 50 in a substantially horizontal direction and opens onto a discharge chamber 20, through an inlet hole 20b arranged on a side wall thereof. As represented in the embodiment of FIG. 2, the discharge chamber 20 is, for example, arranged underneath the first piston housing 14 and fluidically connected thereto through a first suction hole 20a arranged on the top base of the discharge chamber 20.

The first communication duct 3 arranged between the T connector 50 and the inlet hole 20b has a first hydraulic valve 27 intended for regulating the passage of the fluids from the first communication duct 3 to the discharge chamber 20.

The third communication duct 11 extends from the second outlet port 53 of the hydraulic T connector 50 in a substantially horizontal direction (opposite communication duct 3) and opens onto a suction chamber 10, through a further inlet hole 10d arranged on a side wall thereof and in the proximity of its own bottom base. As represented in the embodiment of FIG. 2, the suction chamber 10 is, for example, arranged underneath the second piston housing 12 and fluidically connected thereto through a second suction hole 10a arranged on the top base of the suction chamber 10. The bottom base of the suction chamber 10 has a preparation outlet, here formed by a plurality of nozzles 18, e.g. arranged array-like and fluidically connected to the suction chamber 10. The nozzles 18 vertically extend from the bottom base of the suction chamber 10, parallel to each other, and open onto a bottom surface 81 of the body 1, in a position facing a plurality of wells 33, in the underlying chip 16. Thus, each nozzle 18 opens into a respective well 33.

A further partial diaphragm 10c extends within the suction chamber 10 from the side wall of the suction chamber 10 where the further inlet hole 10d is located and above it. The further partial diaphragm 10c extends in a substantially horizontal direction with respect to the bottom base of the suction chamber and terminates in proximity of the wall of the suction chamber 10 opposite to the starting one, without connecting thereto and thus forming a suction opening 10b. In this way, the further partial diaphragm 10c divides the suction chamber 10 into two further volumes: an air chamber 10e, which develops above the partial diaphragm 10c, and a preparation-conveying chamber 10f, which develops underneath the partial diaphragm 10c. The air chamber 10e and the preparation-conveying chamber 10f are fluidically connected together through the opening 10b.

The third communication duct 11 is further provided with a second hydraulic valve 28, arranged between the suction chamber 10 and the T connector 50, and designed for adjustment of the passage of the fluids from the third communication duct 11 to the plurality of nozzles 18.

The device 1000 further comprises a first ringnut 26 for micrometric movements applied to the first piston 13 and a second ringnut 25 for micrometric movements applied to the second piston 19. The first ringnut 26 and the second ringnut 25 are conformed to enable a fine sliding adjustment of the first piston 13 within the first housing 14 and of the second piston 19 within the second housing 12, respectively.

With reference to FIGS. 3-9, a method for preparing a sample containing biological material using the device 1000 of FIG. 2 will be described hereinafter. In particular, the illustrated method regards preparation of a biologic sample for RT-PCR analysis of DNA.

Figure 9:
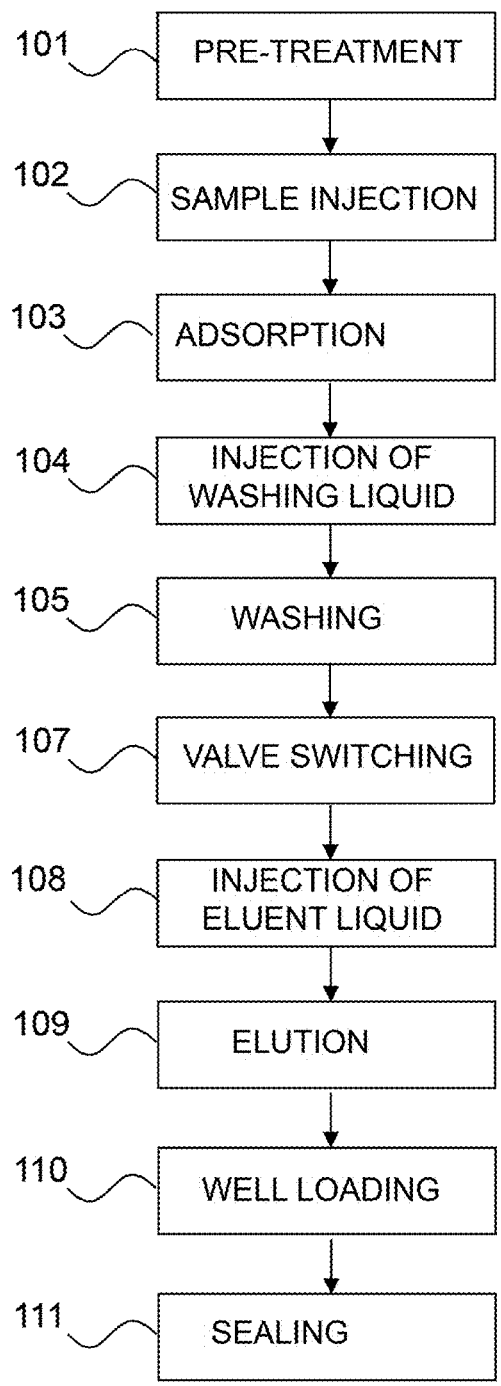
FIG. 9 is a flowchart of the method for preparing the sample.

With reference to FIG. 9, initially a raw biologic sample from which DNA is extracted, for example a whole-blood sample, is subjected to a pre-treatment step 101, performed outside the device 1000. As is known to a person skilled in the art, the pre-treatment step includes cell lysis, obtained, for example, by introducing the raw biologic sample into a hypotonic solution. The pre-treatment step can further comprise digesting the contaminating proteins using suitable enzymes, such as for example proteinase K. At the end of the pre-treatment step 101, the pre-treated sample 21a thus obtained (FIG. 3) is loaded into a first syringe 21. It is also possible to perform the pre-treatment step in the device, but for simplicity, we describe cell lysis before application to the device.

Next, the sample injection step 102 of FIG. 9 is carried out. In detail (FIG. 3), the syringe 21 containing the pre-treated biologic sample 21a is inserted into the second syringe chamber 8, perforating first the outer closing layer 9 and then the diaphragm 30; then the pre-treated sample 21a is injected into the filtering compartment 6.

During the sample injection step 102, the first hydraulic valve 27 is open, and the second hydraulic valve 28 is closed.

Simultaneously or subsequently, the first piston 13 is displaced towards the outside of the body 1, for example using the first ringnut 26. The fluid-tight movement of the first piston 13 within the respective housing 14 creates a negative pressure in the discharge chamber 20, which, by virtue of opening of the first hydraulic valve 27, propagates as far as the filtering compartment 6 fluidically connected thereto, forcing flow of the pre-treated sample 21a into the conveying duct 40, towards the filtering matrix 5; thereby minimizing contamination. It is also possible to perform these steps using positive pressure and changing the relative positions of the pistons.

Next (adsorption step 103 of FIG. 9 and FIG. 4), the pre-treated sample 21a traverses the connection opening 42 and reaches the filtering matrix 5. In this way, the pre-treated sample 21a flows along the entire filtering matrix 5 throughout its length, causing adsorption of the DNA contained in the pre-treated sample 21a on the surface of the filtering matrix 5. In the adsorption step 103, also other interfering materials, such as lipids and proteins, in the pre-treated sample 21a can be partially adsorbed on the surface of the filtering matrix 5.

After the pre-treated sample 21a has traversed the filtering matrix 5 and, consequently, is without the part of DNA and of interfering materials adsorbed by the filtering matrix 5, it exits the filtering compartment 6 through the outlet opening 6a, traverses the second communication duct 4 and, through the T connector 50, passes into the first communication duct 3, finally flowing into the discharge chamber 20. The second valve 28, being closed, prevents the pre-treated sample 21a from accidentally reaching the nozzles 18. At the end of this step, the pre-treated sample 21a, except for the part adsorbed on the filtering matrix 5, is inside the discharge chamber 20.

In the subsequent washing liquid injection step 104 of FIG. 9 (see also FIG. 5), a second syringe 31, containing a washing liquid 31a is introduced into the first syringe chamber 7 and perforates the diaphragm 30. Then the washing liquid 31a is injected into the filtering compartment 6.

Simultaneously or subsequently, the first piston 13 is further displaced towards the outside (top) of the body 1, for example using the first ringnut 26. The movement of the first piston 13 creates a further negative pressure in the discharge chamber 20, which, due to the first hydraulic valve 27 that is open, propagates as far as the filtering compartment 6 fluidically connected thereto, forcing the flow of the washing liquid 31a in the conveying duct 40 towards the filtering matrix 5.

Next (washing step 105 of FIG. 9 and FIG. 6), the washing liquid 31a flows, through the connection opening 42, into the matrix compartment 41. Then, the washing liquid 31a traverses the filtering matrix 5, removing in its passage the interfering substances, such as proteins and lipids, adsorbed on the surface of the filtering matrix 5 during the adsorption step 103.

After traversing the filtering matrix 5, the washing liquid 31a, enriched with the interfering substances removed from the surface of the filtering matrix 5, exits the filtering compartment 6 through the outlet opening 6a, traverses the second communication duct 4, and, through the T connector 50, passes into the first communication duct 3, finally flowing into the discharge chamber 20. It should be noted that the second hydraulic valve 28, being closed, prevents the washing liquid 31a from accidentally reaching the nozzles 18. At the end of this step, all of the washing liquid 31a is contained within the discharge chamber 20.

Next (valve-switching step 107 of FIG. 9), the first hydraulic valve 27 is closed, and the second hydraulic valve 28 is opened.

Afterwards (eluent liquid injection step 108 of FIGS. 9 and 7), an eluent liquid 61a, for example an aqueous solution with low saline concentration (usually TE buffer), is injected into the filtering compartment 6 using a third syringe 61 introduced into the first syringe chamber 7.

Simultaneously or subsequently, a second piston 19 is displaced towards the outside of the body 1, for example using the second ringnut 25. The movement of the second piston 19 creates a negative pressure in the suction chamber 10, which, by virtue of the second hydraulic valve 28 being open, propagates as far as the filtering compartment 6 fluidically connected thereto, forcing the flow of the eluent liquid 61a towards the filtering matrix 5.

Then (elution step 109 of FIG. 9 and FIG. 8), the eluent liquid 61a traverses the filtering matrix 5 throughout its length, eluting the DNA previously adsorbed during the adsorption step 105 and thus causing the previously absorbed DNA to elute into the buffer.

Next (well loading step 110 of FIG. 9 and FIG. 8), the eluent liquid 61a, now containing the eluted DNA and forming a prepared sample 70, proceeds, traverses the second communication duct 4, the T connector 50, and the third communication duct 11, reaching the nozzles 18, and from these, by capillarity action and gravity, flows into the corresponding wells 33.

It should be noted that the off condition of the first hydraulic valve 27 prevents the prepared sample 70 from accidentally reaching the discharge chamber 20. In this way, the prepared sample 70 is available within the plurality of wells 33.

Finally (sealing step 111), the clips 29 are removed, the cartridge 2 is detached from the body 1, and a liquid sealant, for example mineral oil, is poured on the wells 33 to obtain sealing of the prepared sample within the wells 33. The cartridge, with the prepared sample 70 contained therein, can thus be introduced in a thermal cycler (not shown) for performing the RT-PCR analysis, in a per se known manner not described in detail.

Figure 10:
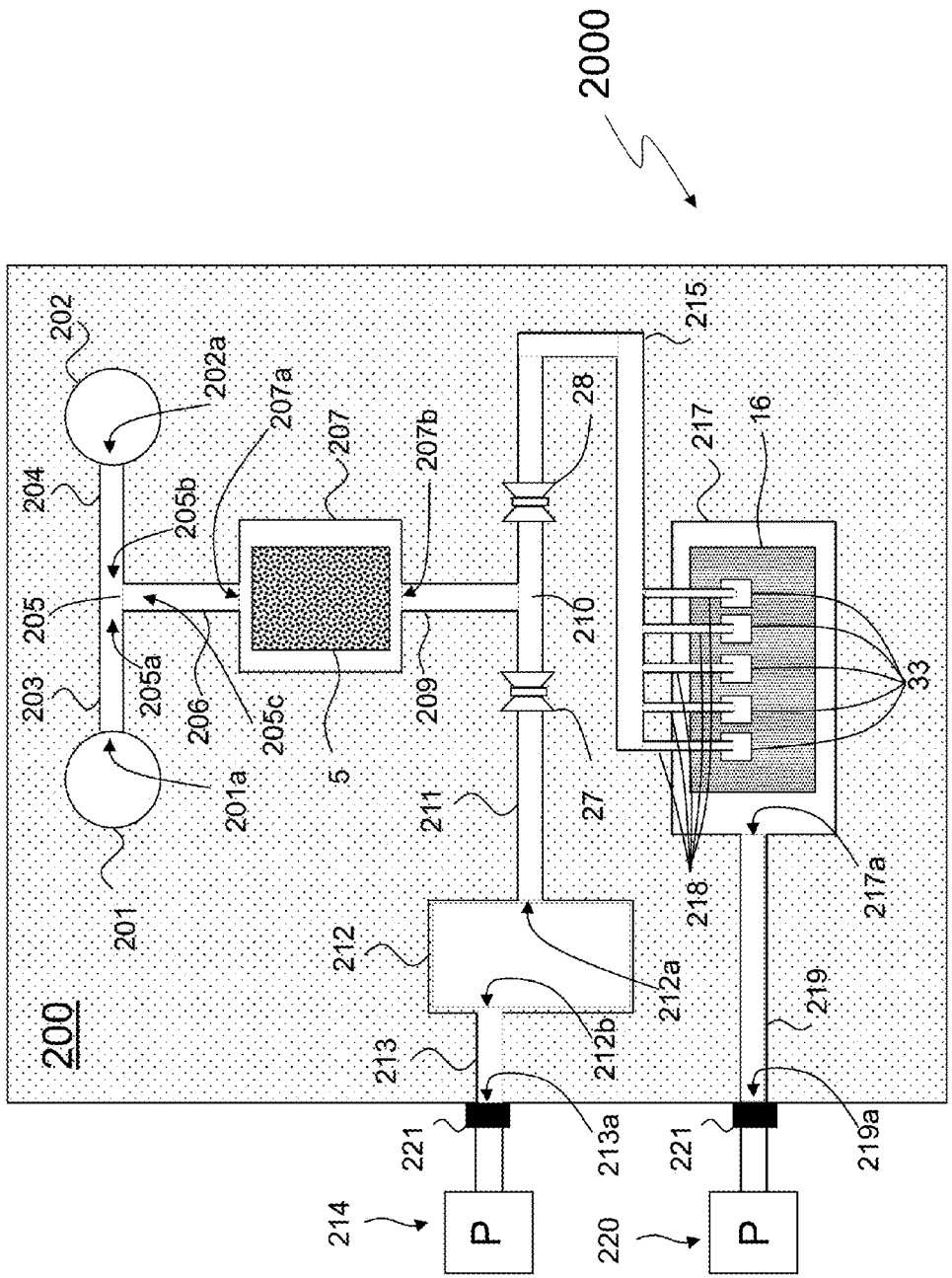
FIG. 10 is a plan section of another embodiment of a device for preparing a sample containing biological material.

FIGS. 10 and 11 show a different embodiment of the device 1000 of FIG. 2. Here, a device 2000 comprises a body 200 of, for example, partially or completely transparent plastic material, such as transparent polycarbonate obtained by molding and shaping techniques. The body 200 has, for example, the shape of a parallelepiped and a substantially planar development, where the vertical dimension is considerably smaller than the two horizontal dimensions (e.g., generally flat), for example about 4×8×1 cm³. Through moulding and shaping within the body 200, a hydraulic circuit for movement of fluids is obtained, the structure whereof is described in detail hereinafter.

The body 200 comprises a first and a second inlet wells 201, 202, each forming a fluid inlet. The first and second inlet wells 201 and 202 are open outwards on the top surface 270 of the body 200 and are coated or covered prior to use with an outer closing layer (not shown).

A first delivery hole 201a is arranged on the lateral (side) surface of the first inlet well 201, and a first delivery duct 203 extends therefrom in a horizontal direction and is connected to a first inlet port 205a of a first hydraulic T connector 205. A second delivery hole 202 is arranged on the lateral surface of the second inlet well 202, and a second delivery duct 204 extends therefrom in a horizontal direction and is connected to a second inlet port 205b of the first hydraulic T connector 205.

A third delivery duct 206 extends in a horizontal direction from an outlet port 205c of the first hydraulic T connector 205 and is connected to a third delivery hole 207a arranged on the lateral surface of a filtering compartment 207, to the inside whereof the filtering matrix 5 is fixed. The filtering compartment 207 is further provided with an outlet hole 207b, for example arranged opposite to the inlet hole 207a, and a first communication duct 209 extends therefrom in a horizontal direction and is connected to an inlet of a second hydraulic T connector 210.

A discharge duct 211 extends in a horizontal direction from the second hydraulic T connector 210 and opens onto a discharge chamber 212, through an inlet hole 212a arranged on the lateral surface thereof. The discharge chamber 212 is further provided on its own lateral surface with a first suction hole 212b; a first intake duct 213 extends therefrom in a horizontal direction and terminates on a first inlet hole 213a available on the lateral surface of the body 200. Outside the body 200, a first pumping unit 214 is connected to the first inlet hole 213a via connectors 221.

Moreover the second hydraulic valve 27 is arranged on the discharge duct 211 for adjusting the passage of the fluids from the discharge duct 211 to the discharge chamber 212.

A preparation duct 215 extends in a horizontal direction from the second hydraulic T connector 210 and has a preparation outlet, here formed by a plurality of injection ducts 218, fluidically connected to the preparation duct 215. The injection ducts 218 extend in a horizontal direction, parallel to each other, and end within a chip-housing chamber 217 designed to house the chip 16. The chip 16 is fixed to the bottom of the chip-housing chamber 217, for example, by gluing or by friction fit. The injection ducts 218 are configured to terminate or have openings (not shown) facing the wells 33.

The chip housing chamber 217 has, on its own lateral surface, a second suction hole 217a; a second intake duct 219 extends therefrom and ends on a second inlet hole 219a, which is available on the lateral surface of the body 200 and connects the second intake duct 219 with the outside of the body 200. A second pumping unit 220 is connected to the second inlet hole 219a via connectors 221. In this embodiment, the first and second pumping units 214, 220 form fluid moving means.

The first hydraulic valve 28 is here arranged on the preparation duct 215, between the injection ducts 218 and the second T connector 210.

The method for preparing a sample containing biological material using the device 2000 of FIGS. 10 and 11 is similar to the one described for the device 1000 of FIG. 2. It is merely pointed out that, in the present case, the movement of the liquids as far as the injection ducts 218 takes place only as a result of the negative pressure generated by the pumping units 214 and 220, without the aid of gravity. In addition, the second pumping unit 220 generates a negative pressure directly within the chip-housing chamber 217.

After loading the prepared sample, it is possible also in this case to seal the wells 33 with e.g., oil to prevent evaporation during thermal cycling. In this case, a further inlet well (not shown) may be arranged near the preparation loading chamber 217 and connected to the preparation duct 215 or directly to the injection ducts 218. Thus, the oil may be conveniently added via such an inlet well.

Finally, after loading and possible sealing the wells 33 and disconnection of the external pumping units 214, 220, the body 200 is inserted in a thermal cycler (not shown) for subsequent RT-PCR analysis based upon detection of fluorescence thanks to the transparency of the material of the body 200.

FIG. 12 shows a detail of a different embodiment. Here, a device 3000 has a general structure similar to that of the device 1000 of FIG. 2, except for the hydraulic valves 27 and 28, which are replaced by respective automatic hydraulic valves here formed by balls 303c, 311a movable within the first and third communication ducts, here designated respectively by 300, 311. For the rest, the device 3000 is the same as the device 1000 of FIG. 2, so that common parts are omitted.

In this embodiment, the first communication duct 303 extends partially within the discharge chamber 20 and is here provided with a discharge hole 303a facing the bottom base of the discharge chamber 20. The portion of the first communication duct 303 within the discharge chamber 20 is provided, at its own terminal section, with a first partial diaphragm 303b. The first partial diaphragm 303b is arranged transverse to the longitudinal direction of the first communication duct 303, and obstructs the terminal section only partially, forming a ball-suction hole 303e and a stop for the mobile ball 303c.

The ball-suction hole 303e and the discharge hole 303a have a smaller cross-section than the overall dimensions of the ball 303c so that the latter cannot exit the first communication duct 303 through them.

The first communication duct 303 is moreover provided with a second partial diaphragm 303d arranged upstream of the discharge hole 303a, on a section transverse to the longitudinal direction of the first communication duct 303. The second partial diaphragm 303d obstructs the section only partially, forming a connection opening 303f and defining a stop for the mobile ball 303c.

The cross-section of the first communication duct 303 and the diameter of the mobile ball 303c are chosen so as to enable rolling of the mobile ball 303c within the first communication duct 303, at least in the stretch comprised between the first and second diaphragms 303b, 303d.

In the embodiment in FIG. 12, the third communication duct 311 has a connection hole 311*d*, and a further ball-suction hole 311*e* extends partially within the suction chamber 10. A partial diaphragm 310*c* extends within the suction chamber 30, underneath the third communication duct 311, similarly to the further partial diaphragm 10*c* of FIG. 2. In detail, in FIG. 12, the portion of the third communication duct 311 internal to the suction chamber 10 extends parallel and above the partial diaphragm 310*c* and is in contact with the top surface of the partial diaphragm throughout its own extension.

The third communication duct 311 has a third partial diaphragm 311*c* at its terminal section. The third partial diaphragm 311*c* is arranged transversely to the longitudinal direction of the third communication duct 311, only partially obstructs its terminal section, forming the further ball suction hole 311*e*, and forms a stop for the further ball 311*a*. The further ball suction hole 311*e* has a surface smaller than the overall dimensions of the further mobile ball 311*a*.

The connection hole 311*d* (formed both in the third communication duct 311 and the underlying partial diaphragm 310*c*) faces the bottom base of the suction chamber 10 and has a cross-section smaller than the overall dimensions of the further mobile ball 311*a*. The connection hole 311*d* fluidically connects the preparation conveying chamber 10*f* and the third communication duct 311.

The third communication duct 311 has a fourth partial diaphragm 311*b* arranged on a section transverse to the longitudinal direction of the third communication duct 311 and obstructing the section only partially, forming a further connection opening 311*f* and defining a stop for the further mobile ball 311*a*. The cross-section of the third communication duct 311 and the diameter of the ball 311*a* are chosen so as to enable rolling of the further mobile ball 311*a* within the third communication duct 311.

Operation of the device 3000 of FIG. 12 will be described limitedly to actuation of the hydraulic valves. In particular, during the steps of sample injection 102, adsorption 103, washing liquid injection 104, and washing 105 of FIG. 9, wherein the first piston 13 (FIG. 2) is extracted (as represented in FIG. 12 by the arrow A) and a negative pressure is produced inside the suction chamber 20, the mobile ball 303*c* is pushed towards the ball suction hole 303*e* (dashed line position). Consequently, the discharge chamber 20 is fluidically connected to the first communication duct 303 through the discharge hole 303*a*. This condition is equivalent to opening the first hydraulic valve 27 in FIG. 2.

At the same time, the negative pressure in the discharge chamber 20 propagates to the third communication duct 311, causing movement of the further ball 311*a* towards the third partial diaphragm 311*b* (dashed line position).

Here, the further ball 311*a* totally obstructs the further connection opening 311*f*, similarly to closing the second hydraulic valve 28 of FIG. 2.

In a dual way, in the steps of eluent liquid injection 108, elution 109, and well loading 110 of FIG. 9, wherein the second piston 19 (FIG. 2) is extracted (as represented in FIG. 12 by the arrow B), the negative pressure within the suction chamber 10 causes displacement of the further mobile ball 311*a* until it comes into contact with the third partial diaphragm 311*c* (wherein the further mobile ball 311*a* is represented by a solid line), obstructing the further suction hole 311*e*.

Consequently, fluidic connection is obtained between the third communication duct 311 and the suction chamber 10, corresponding to opening the second hydraulic valve 28 of FIG. 2.

At the same time, the negative pressure in the suction chamber 10 causes displacement of the ball 303*c* towards the second partial diaphragm 303*d* (position of the mobile ball 303*c* represented with a solid line), obstructing the further connection opening 303*f*, in a way similar to closing the first hydraulic valve 27 in FIG. 2.

As is evident to a person skilled in the art, the hydraulic valves 27 and 28 of FIG. 10 may be made in a similar way.

Figure 13:
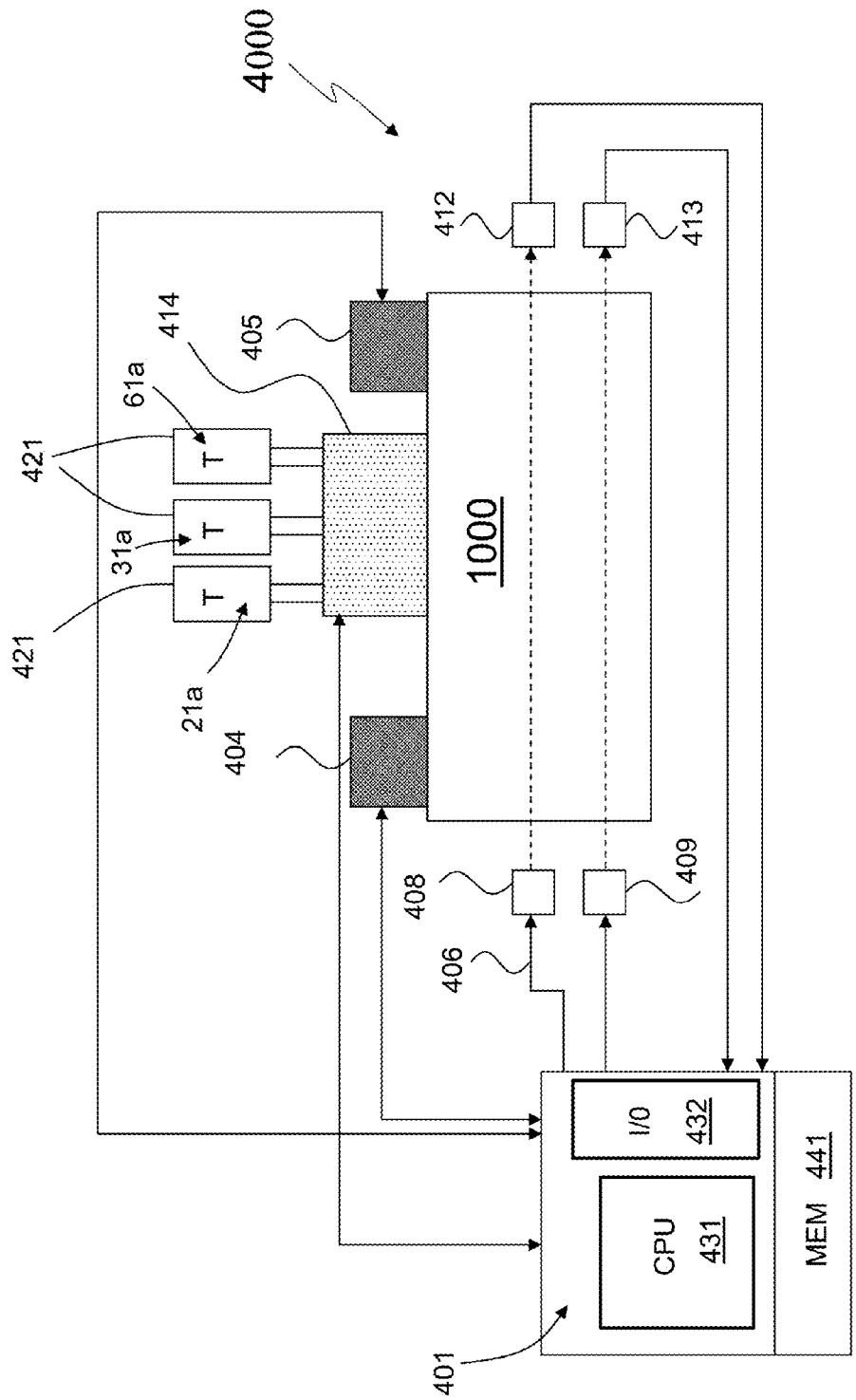
FIG. 13 shows an apparatus for performing a biological analysis.

FIG. 13 illustrates an apparatus 4000 for conducting clinical analyses including the previously described device 1000. The apparatus 4000 comprises electric actuators 404 and 405, an electronic device 401, fluid containing means 421, and an injection module 414. The electronic device 401 is, for example, provided with a processing unit 431, an input/output unit 432, and a memory unit 441. The fluid containing means are, for example, formed by three reservoirs 421, configured to contain the pre-treated biologic sample 21*a*, the washing liquid 31*a*, and the eluent liquid 61*a*. The injection module 414 is configured so as to selectively and fluidically connecting each of the three reservoirs 421 and the fluid inlet of the device 1000. The connection can be controlled electrically, for example by controlling solenoid valves comprised in the injection module 414 but not shown.

The apparatus 4000 is further provided with means for optical detecting the presence or absence of the fluid within the fluidic circuit, here formed by a first laser source 408 and a corresponding first sensing photodiode 412, and by a second laser source 409 and a corresponding second sensing photodiode 413. The first laser source 408 and the first sensing photodiode 412 are positioned so as to intercept the first communication duct 3 in a transverse direction (FIG. 2). The second laser source 409 and the second sensing photodiode 413 are positioned so as to intercept the third communication duct 11 in a transverse direction (FIG. 2). The first laser source 408 and the first sensing photodiode 412 are configured to detect and electrically communicate the end of travel of the pre-treated biologic sample 21*a* and of the washing liquid 31*a* in the first communication duct 3 (FIG. 2) by virtue of the transparency of the body 1. Likewise, the second laser source 409 and the corresponding second sensing photodiode 413 are configured for detecting and electrically communicating end of travel of the prepared sample 70 (FIG. 8) in the third communication duct 11.

The electronic device 401 is connected to and controls the electric actuators 404 and 405, the laser sources 408 and 409, the sensing photodiodes 412 and 413, and the injection module 414.

A software may be loaded into the memory 441 and may be executed by the processing unit 431 so as to actuate the electric actuators 404, 405, the first and second laser sources 408, 409, the first and second sensing photodiodes 412 and 413, and the injection module 414 in order to carry out the steps of the method of FIG. 9 in an automatic way.

In particular, temporal scanning of the steps of the method of FIG. 9 is controlled by the electronic device 401 on the basis of the signals supplied by the sensing photodiodes 412, 413.

As is evident to a person skilled in the art, the apparatus 4000 may comprise, instead of the device 1000, the device 2000 or 3000 of FIGS. 10, 12.

The described solutions present numerous advantages. In fact, they can be integrated with expert systems that can be used not only in the specialist field but also in the doctor's surgery or at home (in the case of self-diagnosis).

Moreover, by performing the operations of adsorption, washing, and elution within a single body, closed to the external environment and thus not subject to contamination, these devices are able to ensure a high degree of purity of the prepared sample, thus increasing the diagnostic reliability. In addition, the execution of the operations in sequence within a same device enables reduction of the analysis times.

The device can operate also on reduced volumes of sample and thus of reagents, thus reducing the costs of analysis and increasing the yield. In fact, treatment of the liquids within a same filtering compartment enables reduction of the leakages typical of known kits, no longer requiring transfer of the intermediate product to different test tubes or Eppendorf® tubes.

The proposed solutions meet the requirement of purity, understood both as presence in solution of the considered nucleic acid and as absence of contaminating substances, which, binding to or interfering with the reagents in solution, could modify the results of the subsequent experiment (PCR, RT-PCR, sequencing, restriction digestion, etc.).

Furthermore, the described device eliminates the risks of contamination of the external environment, since the steps of adsorption, washing, and elution, as well as subsequent analysis are carried out within the same device.

The described devices can be pre-arranged so as to be operated in a semiautomatic or automatic way using appropriate machinery, as explained above.

In the solution of FIG. 2, loading of the wells 33 occurs without any discontinuity at the end of the elution step, as a result of transfer of the prepared sample 70 through the second communication duct 4, the third communication duct 11, and the injection ducts 18.

In the solution of FIG. 10, the device 2000 can be advantageously and directly loaded into the thermal cycler, without requiring separate operations for opening the device, and extracting and transferring the cartridge 2, thus eliminating any possible remaining risks of contamination or errors of transfer and/or loading of the silicon chip 16.

Numerous modifications and variations may be made to the device and the method described herein, all of which fall within the scope of the attached claims.

For example, in the solution of FIG. 2, the means for fixing the body 1 to the cartridge 2 may be different from what is shown; for example, they may be formed by mechanical retention systems, such as screwed brackets, elements for mutual engagement, or other elastic elements.

The fluid movement means may be implemented in a different way, as elements internal or external to the body 1; for example, in the solution of FIG. 2 pumping units may be provided similar to those shown in FIG. 10, but other types of pumping elements may be used, for instance, electrically controlled pumps, which may be connected to the device 1000, 2000, 3000 prior to use, or introduced into a suitable automatic machine for controlling the analysis (not shown).

In FIG. 2, the two suction units 13-14, and 12-19 may be arranged horizontally, with the first and second piston housings 13 and 14 arranged alongside the discharge chamber 20 and the suction chamber 10, respectively.

According to a variant, the first and second hydraulic valves 27, 28 of the device 1000 of FIG. 2 can be electrically controlled, with a control module 82 (represented dashed) configured to generate respective opening and closing signals. Of course, also the device 2000 may be provided with electrically controlled hydraulic valves 27, 28.

In FIG. 2, the first and third communication ducts 3, 11 may be implemented so as to exploit gravity, with a negative slope from the hydraulic T connector 50 to the discharge chamber 20 and the suction chamber 10, respectively.

In FIG. 2, the body 1 may comprise a single syringe chamber instead of the chambers 7, 8. In this case, the pre-treated sample 21a, the washing liquid 31a, and the eluent liquid 61a are all injected through a same syringe chamber. Alternatively, three syringe chambers may be provided, one for the pre-treated sample 21a, one for the washing liquid 31a, and one for the eluent liquid 61a. Additional buffer chambers can be provided if sample preparation requires additional steps. Similar variants apply to the devices 2000, 3000.

In the embodiment of FIG. 12, moreover, the limitation of the travel of the balls 303c, 311a could be obtained, instead of with the stop elements 303b, 303d, 311b, 311c, by providing the communication ducts 303, 311 with a non-uniform cross-section, greater in the area of movement of the balls, and smaller elsewhere, or arranging necks (partial or annular constrictions) in the communication ducts.

The invention claimed is:

1. A device for preparing biologic samples, comprising:
a fluid inlet;
a filtering compartment, connected to said fluid inlet and accommodating a filtering matrix and an adsorption agent and including a partial diaphragm, a perimeter, and an outlet opening, the partial diaphragm extending from a side wall of the filtering compartment and dividing the filtering compartment into a conveying duct that extends above the partial diaphragm and a matrix compartment that extends underneath the partial diaphragm, the partial diaphragm defining a fluidic connection opening for fluidically connecting the conveying duct and the matrix compartment, the fluidic connection opening and the outlet opening being arranged in opposite areas of the perimeter of the filtering compartment;
a fluidic circuit connected downstream of said filtering compartment and including a discharge circuit and a loading circuit;
a discharge chamber, connected downstream of said discharge circuit;
a preparation outlet, connected downstream of said loading circuit; and
a chip of semiconductor material having at least one well facing said preparation outlet.

2. The device according to claim 1, further comprising pumping units connected to said fluidic circuit and configured to fluidically connect said filtering compartment alternatively to said discharge circuit or to said loading circuit.

3. The device according to claim 2, wherein said pumping units comprise a first pumping unit connected to the discharge circuit and a second pumping unit, connected to said loading circuit.

4. The device according to claim 3, wherein the first and second pumping units are suction units formed by a respective piston mobile in a respective piston housing chamber and by a respective ringnut designed for fine movement of said respective piston of said respective suction unit.

5. The device according to claim 1, further comprising a first valve means, arranged along said loading circuit, for selectively fluidically connecting the filtering compartment to said preparation outlet and a second valve means, arranged along said discharge circuit, for selectively fluidically connecting the filtering compartment to said discharge chamber.

6. The device according to claim 5, wherein said first and second valve means comprise electrically controlled valves connected to an external control module.

7. The device according to claim 5, wherein said first valve means comprise first and second abutment elements and a first ball movable within said loading circuit . . . and a second ball movable within said discharge circuit between the third and fourth abutment elements.

8. The device according to claim 1, further comprising:
a body that is at least partially transparent, said fluid inlet, said filtering compartment, said fluidic circuit, said discharge chamber, and said preparation outlet being formed within said body.

9. The device according to claim 8, comprising a cartridge including a support that houses said chip.

10. The device according to claim 9, wherein said body is arranged above said cartridge, the device further comprising fixing means for fixing said body and said cartridge together.

11. The device according to claim 10, wherein said body comprises a top surface and a bottom surface, said fluid inlet opening on the top surface and said preparation outlet opening on the bottom surface, said filtering compartment is arranged underneath the fluid inlet and said fluidic circuit is arranged underneath said filtering compartment.

12. The device according to claim 11, wherein said fluid inlet comprises:
at least one syringe chamber configured to accommodate an injection syringe and arranged above said filtering compartment; and
a perforatable diaphragm, said syringe chamber and said filtering compartment being separated by the perforatable diaphragm.

13. The device according to claim 8, wherein said body is flat, and said fluid inlet, said filtering compartment, said fluidic circuit, said preparation outlet, and said discharge chamber are arranged laterally side-by-side.

14. The device according to claim 13, wherein said body accommodates the chip of semiconductor material comprising at least one well facing the preparation outlet.

15. An apparatus for conducting biological analyses, comprising:
a device including:
a fluid inlet;
a filtering compartment, connected to said fluid inlet and accommodating a filtering matrix and an adsorption agent;
a fluidic circuit connected downstream of said filtering compartment and including a discharge circuit and a loading circuit;
a discharge chamber, connected downstream of said discharge circuit;
a preparation outlet, connected downstream of said loading circuit;
a chip of semiconductor material having at least one well facing said preparation outlet;
a suction chamber fluidically coupled to the preparation outlet, and including a partial diaphragm, a perimeter, and an outlet opening, the partial diaphragm extending from a side wall of the suction chamber and dividing the suction chamber into an air chamber that extends above the partial diaphragm and a preparation-conveying chamber that extends underneath the partial diaphragm, the partial diaphragm defining a fluidic connection opening for fluidically connecting the air chamber and the preparation-conveying chamber, the loading circuit and the fluidic connection opening being arranged in opposite areas of the perimeter of the suction chamber; and
an electronic control unit;

at least one reservoir connected to the fluid inlet by an electrically controllable injection module, an electrically controllable actuator for advancing fluids, and an electrically controllable fluid detecting means for verifying the presence of fluid within said discharge circuit and said loading circuit,
said electronic control unit being connected to, and exchanging instructions and information with, the injection module, the actuators, and the fluid detecting means.

16. The device according to claim 15, further comprising:
a body that is at least partially transparent, said fluid inlet, said filtering compartment, said fluidic circuit, said discharge chamber, and said preparation outlet being formed within said body.

17. The device according to claim 15 wherein said body is flat, and said fluid inlet, said filtering compartment, said fluidic circuit, said preparation outlet, and said discharge chamber are arranged laterally side-by-side.

18. The device according to claim 15, further comprising:
pumping units connected to said fluidic circuit and configured to fluidically connect said filtering compartment alternatively to said discharge circuit or to said loading circuit.

19. A device for preparing biologic samples, comprising:
a fluid inlet;
a filtering compartment connected to said fluid inlet;
a filtering matrix and an adsorption agent accommodated in the filtering compartment;
a fluidic circuit connected downstream of said filtering compartment and including a discharge circuit and a loading circuit;
a discharge chamber connected downstream of said discharge circuit;
a preparation outlet connected downstream of said loading circuit;
a suction chamber fluidically coupled to the preparation outlet, and including a partial diaphragm, a perimeter, and an outlet opening, the partial diaphragm extending from a side wall of the suction chamber and dividing the suction chamber into an air chamber that extends above the partial diaphragm and a preparation-conveying chamber that extends underneath the partial diaphragm, the partial diaphragm defining a fluidic connection opening for fluidically connecting the air chamber and the preparation-conveying chamber, the loading circuit and the fluidic connection opening being arranged in opposite areas of the perimeter of the suction chamber;
a chip of semiconductor material having at least one well facing said preparation outlet;
a first pump connected to the discharge circuit and configured to fluidically connect said filtering compartment to said discharge circuit; and
a second pump connected to said loading circuit and configured to fluidically connect said filtering compartment to said loading circuit.

20. The device according to claim 19, further comprising a first valve arranged along said loading circuit and a second valve arranged along said discharge circuit.

21. The device according to claim 20, wherein said first valve includes first and second abutment elements and a first ball movable within said loading circuit . . . and a second ball movable within said discharge circuit between the third and fourth abutment elements.

22. A device for preparing biologic samples, comprising:
a fluid inlet including at least one syringe chamber configured to accommodate an injection syringe;
a filtering compartment, connected to said fluid inlet and accommodating a filtering matrix and an adsorption agent and including a partial diaphragm, a perimeter, and an outlet opening, the partial diaphragm extending from a side wall of the filtering compartment and dividing the filtering compartment into a conveying duct that extends above the partial diaphragm and a matrix compartment that extends underneath the partial diaphragm, the partial diaphragm defining a fluidic connection opening for fluidically connecting the conveying duct and the matrix compartment, the fluidic connection opening and the outlet opening being arranged in opposite areas of the perimeter of the filtering compartment, said fluid inlet being arranged above said filtering compartment;
a perforatable diaphragm separating the syringe chamber and the filtering compartment;
a fluidic circuit connected downstream of said filtering compartment and including a discharge circuit and a loading circuit;
a discharge chamber, connected downstream of said discharge circuit; and
a preparation outlet, connected downstream of said loading circuit.

23. The device according to claim 22 wherein the perforatable diaphragm is perforatable aluminium layer.

24. The device according to claim 22, further comprising:
a first valve, arranged along said loading circuit and configured to selectively fluidically connect the filtering compartment to said preparation outlet and a second valve, arranged along said discharge circuit and configured to selectively fluidically connect the filtering compartment to said discharge chamber.

25. The device according to claim 22, further comprising:
pumping units connected to said fluidic circuit and configured to fluidically connect said filtering compartment alternatively to said discharge circuit or to said loading circuit.

26. A device for preparing biologic samples, comprising:
a fluid inlet;
a filtering compartment, connected to said fluid inlet, including a partial diaphragm, a perimeter, and an outlet opening and accommodating a filtering matrix and an adsorption agent, the partial diaphragm extending from a side wall of the filtering compartment and dividing the filtering compartment into a conveying duct that extends above the partial diaphragm and a matrix compartment that extends underneath the partial diaphragm, the partial diaphragm defining a fluidic connection opening for fluidically connecting the conveying duct and the matrix compartment, the fluidic connection opening and the outlet opening being arranged in opposite areas of the perimeter of the filtering compartment;
a fluidic circuit connected downstream of said filtering compartment and including a discharge circuit and a loading circuit;
a discharge chamber, connected downstream of said discharge circuit;
a preparation outlet, connected downstream of said loading circuit; and
fluid moving means, connected to said fluidic circuit and configured to fluidically connect said filtering compartment alternatively to said discharge circuit or to said loading circuit.

27. The device according to claim 26 wherein the filtering matrix is silica gel and the absorption agent is chaotropic salt.

28. The device according to claim 26, further comprising:
a body that is at least partially transparent, said fluid inlet, said filtering compartment, said fluidic circuit, said discharge chamber, and said preparation outlet being formed within said body.

* * * * *